(12) United States Patent
Singh et al.

(10) Patent No.: US 9,981,927 B2
(45) Date of Patent: May 29, 2018

(54) PROCESS FOR PREPARATION OF POLYMORPHIC FORM OF MIRABEGRON

(71) Applicant: Lupin Limited, Mumbai (IN)

(72) Inventors: Girij Pal Singh, Pune (IN); Dhananjai Shrivastava, Pune (IN); Paramvir Bhadwal, Pune (IN); Malhari Deoram Bhor, Pune (IN); Suryabhan Prabhakar Dange, Pune (IN); Sonaraj Bholenath Jangam, Pune (IN)

(73) Assignee: LUPIN LIMITED, Mumbai (IN)

( * ) Notice: Subject to any disclaimer, the term of this patent is extended or adjusted under 35 U.S.C. 154(b) by 0 days. days.

(21) Appl. No.: 15/547,835

(22) PCT Filed: Feb. 2, 2016

(86) PCT No.: PCT/IB2016/050513
§ 371 (c)(1),
(2) Date: Aug. 1, 2017

(87) PCT Pub. No.: WO2016/125074
PCT Pub. Date: Aug. 11, 2016

(65) Prior Publication Data
US 2018/0016246 A1 Jan. 18, 2018

(30) Foreign Application Priority Data
Feb. 2, 2015 (IN) .......................... 353/MUM/2015

(51) Int. Cl.
*C07D 277/40* (2006.01)

(52) U.S. Cl.
CPC ........ *C07D 277/40* (2013.01); *C07B 2200/13* (2013.01)

(58) Field of Classification Search
CPC ..................... C07B 2200/13; C07D 277/40
See application file for complete search history.

(56) References Cited

U.S. PATENT DOCUMENTS

| 6,346,532 B1 | 2/2002 | Maruyama et al. |
| 7,342,117 B2 | 3/2008 | Kawazoe |

FOREIGN PATENT DOCUMENTS

| IN | 22/2014 A | 5/2014 |
| IN | 48/2015 A | 11/2015 |
| WO | 2012/156998 A2 | 11/2012 |

OTHER PUBLICATIONS

International Search Report & Written Opinion dated Mar. 23, 2016 (PCT/IB2016/050513).

*Primary Examiner* — Valerie Rodriguez-Garcia
(74) *Attorney, Agent, or Firm* — The Dobrusin Law Firm, PC

(57) ABSTRACT

The present invention is directed to process for preparation of α-form crystal of Mirabegron, (R)-2-(2-aminothiazol-4-yl)-N-(4-(2-((2-hydroxy-2-phenylethyl) amino) ethyl) phenyl) acetamide of formula (1).

9 Claims, 3 Drawing Sheets

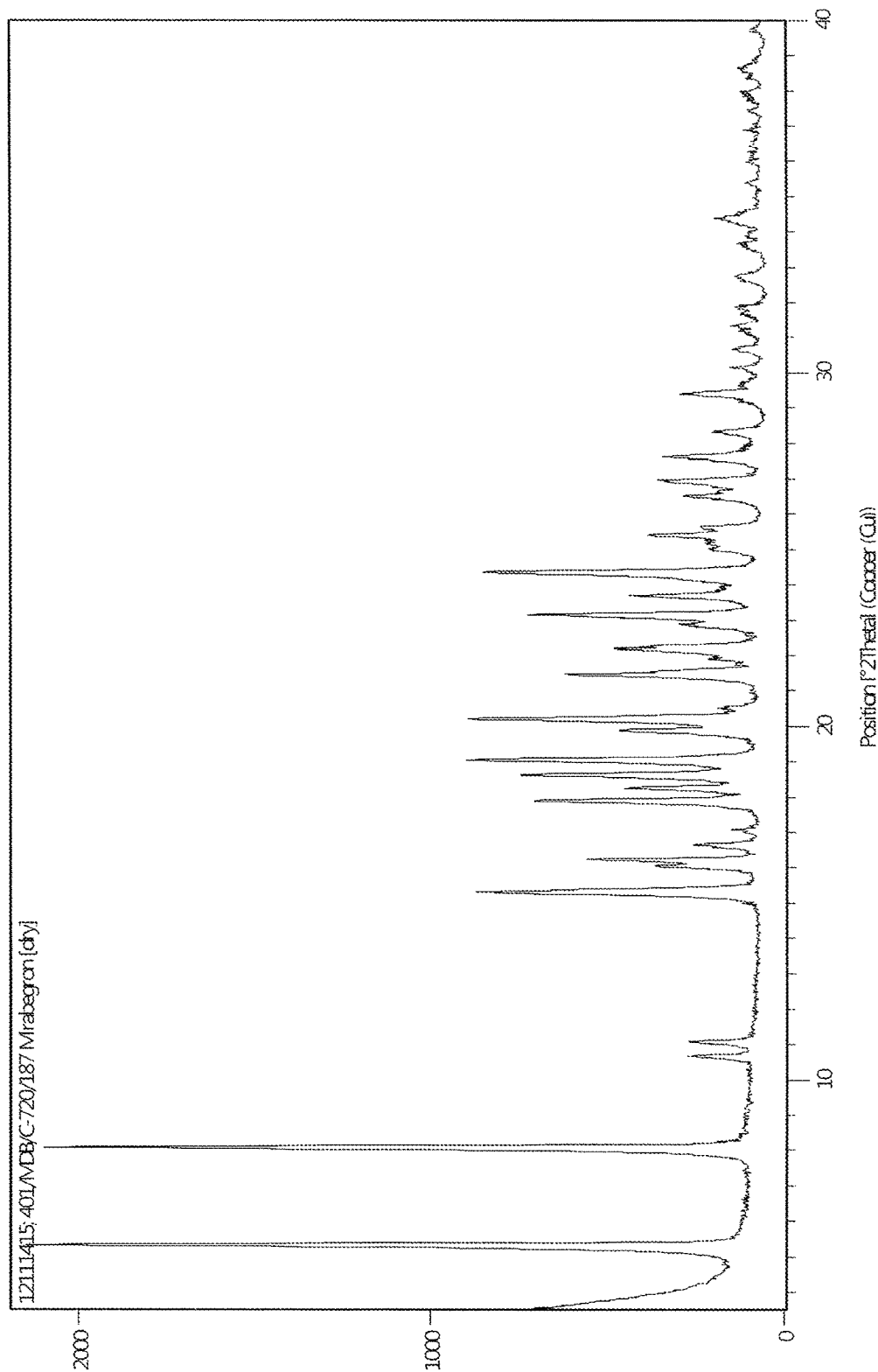
Figure 1: PXRD pattern of α-form crystal of Mirabegron prepared according to Example-3

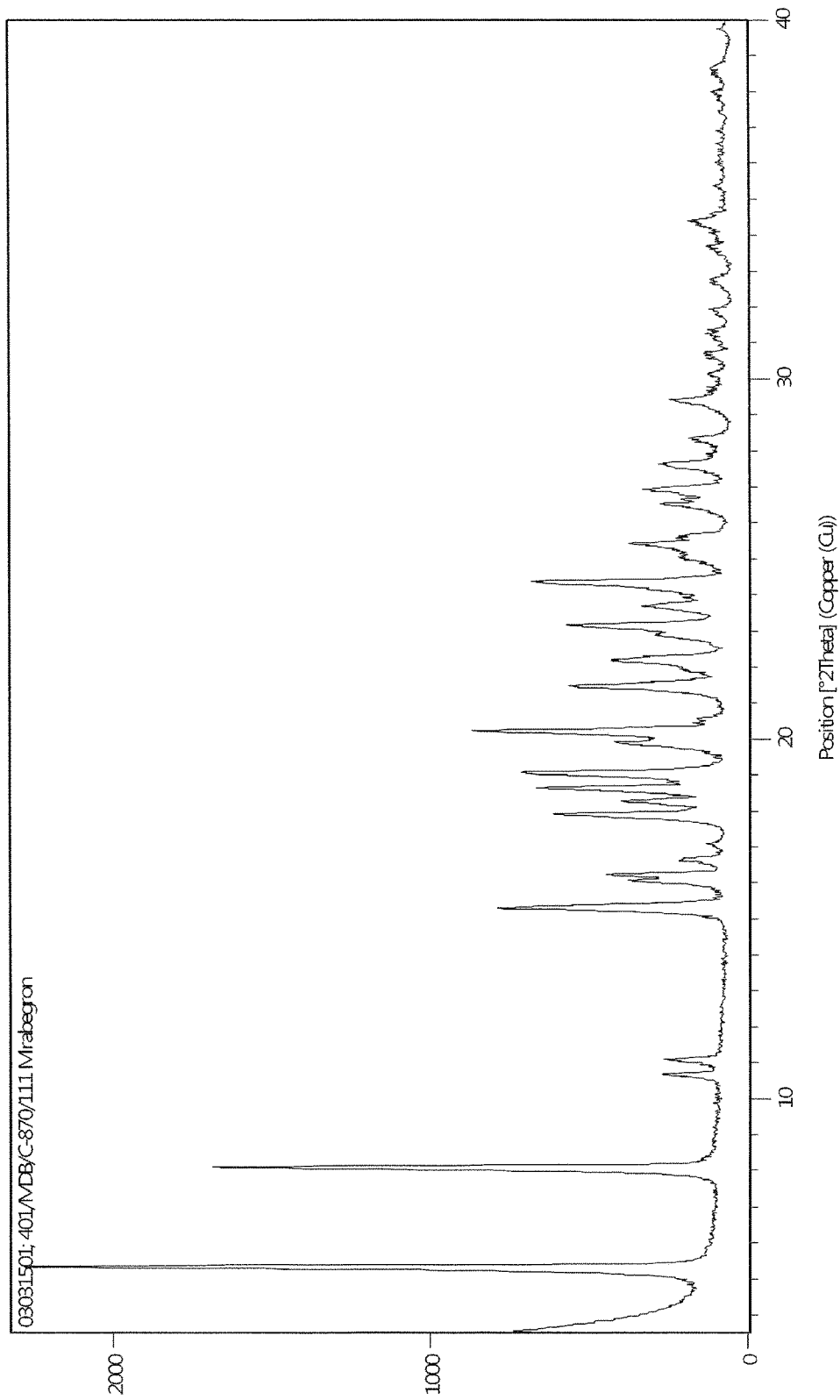
Figure 2: PXRD pattern of α-form crystal of Mirabegron prepared according to Example-9

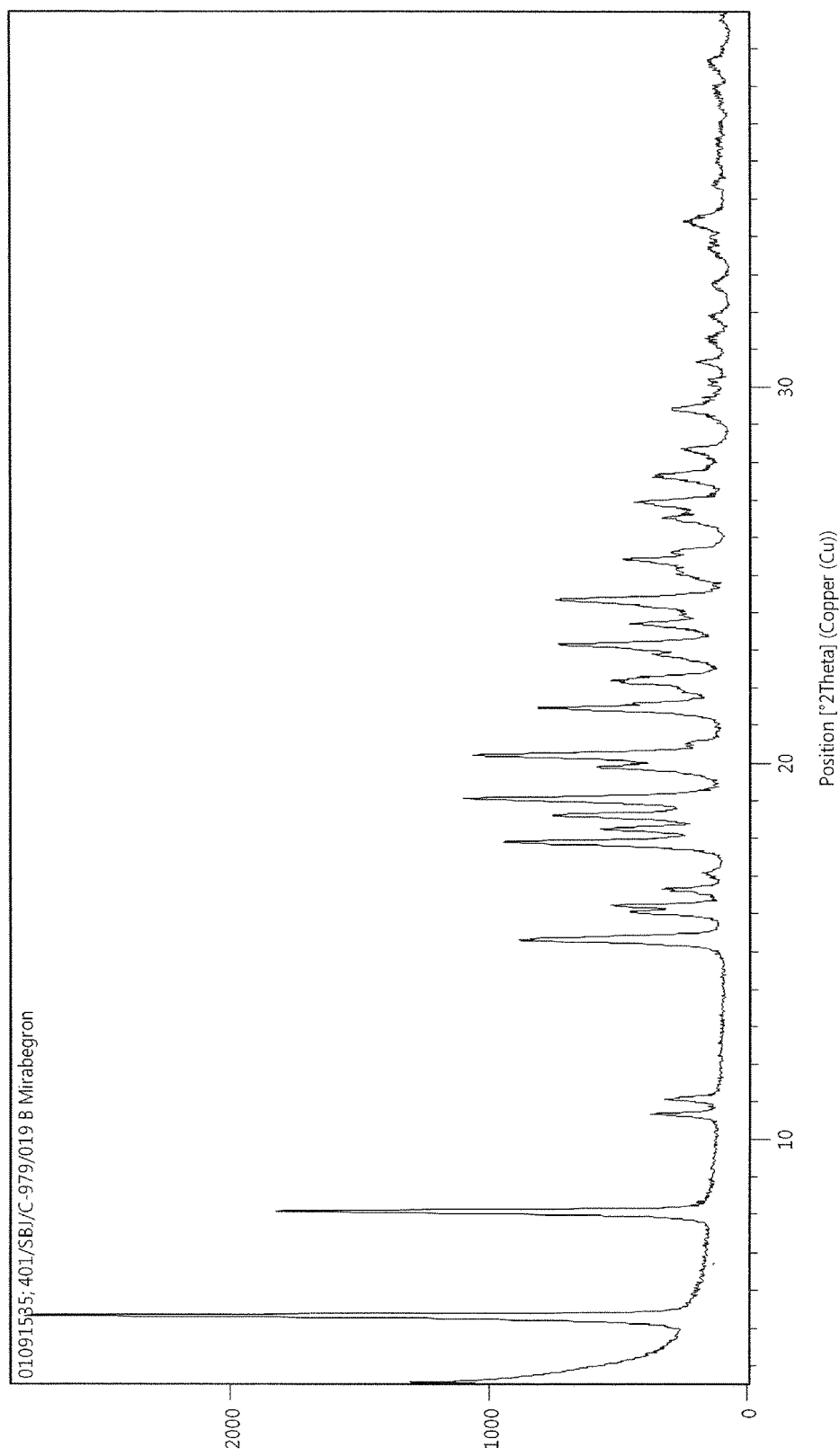
Figure 3: PXRD pattern of α-form crystal of Mirabegron prepared according to Example-10

PROCESS FOR PREPARATION OF POLYMORPHIC FORM OF MIRABEGRON

FIELD OF THE INVENTION

The present invention relates to processes for preparation of α-form crystal of Mirabegron.

BACKGROUND AND THE PRIOR ART

Mirabegron is chemically described as (R)-2-(2-aminothiazol-4-yl)-N-(4-(2-((2-hydroxy-2-phenylethyl) amino) ethyl) phenyl) acetamide or (R)-2-(2-aminothiazol-4-yl)-4'-[2-[(2-hydroxy-2-phenylethyl) amino] ethyl]-acetanilide. It has the chemical formula (1) and is represented by the CAS registration no. 223673-61-8.

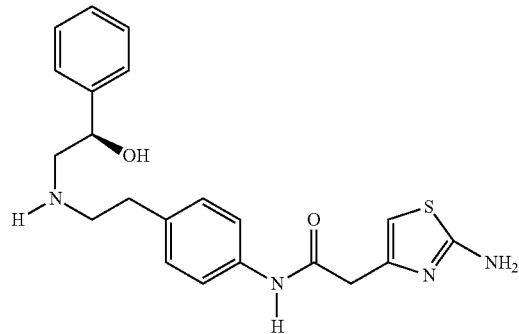

(1)

Mirabegron is an orally active beta-3-adrenoreceptor agonist approved by USFDA for the treatment of overactive bladder (OAB) with symptoms of urge urinary incontinence, urgency, and urinary frequency.

U.S. Pat. No. 6,346,532 B1 (US'532) discloses Mirabegron or a salt thereof and process for its preparation. This patent, however, is silent about the crystal forms of Mirabegron. U.S. Pat. No. 7,342,117 (US'117) patent discloses two crystalline polymorphic forms of Mirabegron, the crystalline α-form and β-form. Said patent discloses the process for preparation of α-form crystal and β-form crystal of Mirabegron.

WO2012/156998A2 discloses processes for the preparation of α-form and β-form crystal of Mirabegron and pharmaceutical composition comprising thereof.

2588/MUM/2012 application discloses a crystalline form of Mirabegron and process for its preparation.

1562/MUM/2014 application discloses process for the preparation of α-form crystal of Mirabegron.

The method for the preparation of α-form crystal and β-form crystal of Mirabegron as per US'117 involves the use of water and ethanol as the only solvent. The process requires gradual or rapid cooling and use of seed material.

The methods for the preparation of crystalline α-form of Mirabegron described in the literature suffer from one or more drawbacks such as reproducibility, use of seed material, less yield and color development during preparation and upon storage which does not lead to an industrially sound process.

Therefore, there exists a need to develop consistent, cost effective and industrially feasible improved processes comprising means of preventing discoloration for the preparation of the hereinabove mentioned polymorphic form of Mirabegron.

OBJECTS OF THE INVENTION

It is an object of the present invention to provide an industrially feasible process for preparation of α-form crystal of Mirabegron comprising means of preventing discoloration during preparation.

It is another object of the present invention to provide a process for preparation of α-form crystal, of Mirabegron in the presence of an antioxidant and/or a chelating agent.

It is yet another object of the present invention to provide the α-form crystal of Mirabegron having reduced particle size for improved bioavailability and bioequivalence.

DESCRIPTION OF THE DRAWINGS

FIG. 1 is an illustration of a powder X-ray diffraction (PXRD) pattern of α-form crystal of Mirabegron prepared according to Example-3.

FIG. 2 is an illustration of a powder X-ray diffraction (PXRD) pattern of α-form crystal of Mirabegron prepared according to Example-9.

FIG. 3 is an illustration of a powder X-ray diffraction (PXRD) pattern of α-form crystal of Mirabegron prepared according to Example-10.

DETAILED DESCRIPTION OF THE INVENTION

The present invention provides a process for the preparation of α-form crystal of Mirabegron.

The present invention further provides an improved process for preparation of α-form crystal of Mirabegron in the presence of an antioxidant and/or a chelating agent.

The term "elevated temperature", unless otherwise specified defines heating either a heterogeneous or homogenous mixture at a temperature from about 30° C. to about boiling point of solvent.

The term "ambient temperature" unless otherwise specified defines the temperature of heterogeneous or homogenous mixture at a temperature of 27° C.±2° C.

In one aspect of the present invention, said process for the preparation of α-form crystal of Mirabegron comprises of;
  (a) preparing a solution of Mirabegron in an organic solvent;
  (b) cooling the solution obtained in step (a) to provide α-form crystal of Mirabegron;
  (c) isolating α-form crystal of Mirabegron; and
  (d) drying the product under reduced pressure.

In step (a) the solution of Mirabegron is obtained by dissolving Mirabegron in an organic solvent. The organic solvent is selected from the group consisting of alkanol, ketone, chlorinated hydrocarbon, ester and nitrile or combinations thereof. The preferred alkanol is methanol, ethanol, propanol, isopropanol, butanol, 2-butanol and pentanol, the preferred ketone is acetone and methyl ethyl ketone, the preferred chlorinated hydrocarbon is dichloromethane, the preferred ester is ethyl acetate and isopropyl acetate, and the preferred nitrile is acetonitrile or mixture thereof, wherein the volume of organic solvent used is 5 to 20 times, preferably 10 to 15 times of the Mirabegron. The preferred organic solvents of the present invention are methanol, ethanol, isopropanol, acetone, dichloromethane or mixtures thereof.

The dissolution process may involve heating the reaction mass to about 40° C. to about 80° C., preferably to about 50° C. to about 70° C., more preferably to about 60° C. to about 75° C.

The solution of Mirabegron obtained in step (a) is micron filtered to obtain a solution free of unwanted particles.

The solution obtained in step (a) is cooled to about −5° C. to about 30° C. to produce α-form crystal of Mirabegron. More preferably the solution is cooled to about 0° C. to about 5° C. to produce α-form crystal of Mirabegron.

The isolation of α-form crystal of Mirabegron in step (c) is done by techniques known in the art such as decantation, filtration by gravity or suction or centrifugation. The α-form crystal of Mirabegron isolated in step (c) is dried at a suitable temperature and pressure for a suitable time.

In a preferred aspect of the present invention, said process for the preparation of α-form crystal of Mirabegron comprises of:
(a) mixing Mirabegron with a mixture of at least two organic solvents selected from the group consisting of alkanol, ketone, chlorinated hydrocarbon, ester and nitrile;
(b) adding an antioxidant and/or a chelating agent to the mixture in step (a);
(c) heating the mixture in step (b) to obtain a solution;
(d) cooling the solution obtained in step (c) to form α-form crystal of Mirabegron;
(e) isolating α-form crystal of Mirabegron; and
(f) drying the isolated α-form crystal of Mirabegron under reduced pressure.

In step (a) Mirabegron is mixed with a mixture of at least two organic solvent selected from the group consisting of alkanol, ketone, chlorinated hydrocarbon, ester and nitrile. The preferred alkanol is methanol, ethanol, propanol, isopropanol, butanol, 2-butanol and pentanol, the preferred ketone is acetone and methyl ethyl ketone, the preferred chlorinated hydrocarbon is dichloromethane, the preferred ester is ethyl acetate and isopropyl acetate, and the preferred nitrile is acetonitrile wherein the volume of organic solvent used is 5 to 20 times, preferably 10 to 15 times of the Mirabegron. The preferred alkanol of the present invention is a mixture of isopropanol and methanol wherein the ratio of methanol to isopropanol (volume/volume) is 1:8; preferably the ratio is 1:4.

In step (b), an antioxidant and/or a chelating agent are added to the reaction mixture obtained in step (a). The antioxidant is selected from group consisting of hydrogen donating antioxidants, such as phenolic antioxidants more preferably butylated hydroxy toluene (BHT), butylated hydroxy anisole (BHA), α-tocopherol, tocopheryl acetate and a mixture thereof. The preferred antioxidant of the present invention is butylated hydroxy anisole. In a preferred aspect of the invention, the chelating agent is ethylenediamine tetra acetic acid or a salt thereof.

In step (c), the reaction mixture of step (b) is heated to about 40° C. to about 90° C., preferably to about 50° C. to about 80° C., more preferably to about 60° C. to about 75° C. to obtain the solution of step (c). The solution of step (c) is optionally micron filtered to make it clear, free of unwanted particles. The solution obtained in step (c) is cooled to about −5° C. to about 30° C., more preferably the solution is cooled to about 0° C. to about 5° C. to produce α form crystal of Mirabegron.

In step (e), the α-form crystal of Mirabegron is isolated by techniques known in the art such as decantation, filtration by gravity or suction or centrifugation. In step (f), the α-form crystal of Mirabegron is dried at a suitable temperature and pressure for a suitable time. The suitable temperature for drying is about 30° C. to about 70° C., preferably is about 50° C. to about 60° C., and more preferably is about 40° C. to about 50° C.

In another preferred aspect of the present invention, said process for the preparation of α-form crystal of Mirabegron comprises of:
(a) mixing Mirabegron with a mixture of at least two organic solvents selected from the group consisting of alkanol, ketone, chlorinated hydrocarbon, ester and nitrile;
(b) adding an antioxidant and/or a chelating agent to the mixture of step (a);
(c) heating the mixture of step (b) to obtain a solution;
(d) cooling the solution obtained in step (c) to form α-form crystal of Mirabegron;
(e) isolating the α-form crystal of Mirabegron formed in step (d);
(f) drying the isolated α-form crystal of Mirabegron from step (e) under reduced pressure; and
(g) milling the dried α-form crystal of Mirabegron from step (f).

In step (a) Mirabegron is mixed with a combination of at least two organic solvents selected from the group consisting of alkanol, ketone, chlorinated hydrocarbon, ester and nitrile. The preferred alkanol is methanol, ethanol, propanol, isopropanol, butanol, 2-butanol and pentanol, the preferred ketone is acetone and methyl ethyl ketone, the preferred chlorinated hydrocarbon is dichloromethane, the preferred ester is ethyl acetate and isopropyl acetate, and the preferred nitrile is acetonitrile wherein the volume of organic solvent used is 5 to 20 times, preferably 10 to 15 times of the Mirabegron. The preferred alkanol of the present invention is a mixture of isopropanol and methanol wherein the ratio of methanol to isopropanol (volume/volume) is 1:8; preferably the ratio is 1:4.

In step (b), an antioxidant and/or a chelating agent are added to the reaction mixture obtained in step (a). The antioxidant is selected from group consisting of hydrogen donating antioxidants, such as phenolic antioxidants more preferably butylated hydroxy toluene (BHT), butylated hydroxy anisole (BHA), α-tocopherol, tocopheryl acetate and a mixture thereof. The preferred antioxidant of the present invention is butylated hydroxy anisole. In a preferred aspect of the invention, the chelating agent is ethylenediamine tetra acetic acid or a salt thereof.

In step (c), the reaction mixture of step (b) is heated to about 40° C. to about 90° C., preferably to about 50° C. to about 80° C., more preferably to about 60° C. to about 75° C. to obtain the solution of step (c). The solution of step (c) is optionally micron filtered to make it clear, free of unwanted particles. The solution obtained in step (c) is cooled to about −5° C. to about 30° C., more preferably the solution is cooled to about 0° C. to about 5° C. to produce α form crystal of Mirabegron.

In step (e), the α-form crystal of Mirabegron is isolated by techniques known in the art such as decantation, filtration by gravity or suction or centrifugation. In step (f), the α-form crystal of Mirabegron is dried at a suitable temperature and pressure for a suitable time. The suitable temperature for drying is about 30° C. to about 70° C., preferably is about 50° C. to about 60° C., and more preferably is about 40° C. to about 50° C.

In step (g) the dried α-form crystal of Mirabegron obtained in step (f) is subjected to particle size reduction by milling, using one or more of air jet milling, ball milling, cad milling, and multi milling. Preferably the dried α-form crystal of Mirabegron from step (f) is multi milled followed by cad milling to obtain the reduced particle size of the present invention.

The size of the particles of α-form crystal of Mirabegron is reduced to have a particle size ($d_{90}$) that is not more than 150 μm, more preferably not more than 75 μm. The size of the particles of α-form crystal of Mirabegron is reduced to have a mean particle size ($d_{50}$) that is between about 2 μm and about 50 μm, more preferably between about 5 μm to about 30 μm. The size of the particles of α-form crystal of Mirabegron is reduced to have a particle size ($d_{10}$) that is not less than 5 μm, more preferably not less than 2 μm.

The advantage of reducing the particle size of α-form crystal of Mirabegron is beneficial for production of dosage forms with improved bioavailability and bioequivalence.

In accordance with the present invention, it is found that the addition of a relatively small quantity of an antioxidant and/or a chelating agent during preparation of α-form crystal of Mirabegron renders α-form crystal of Mirabegron stable against discoloration during preparation and/or upon standing/storage. The molar ratio of the antioxidant and/or a chelating agent to that of the input mirabegron used in the processes of the present invention preferably ranges from about 0.001 to about 0.1 moles, more preferably ranges from about 0.01 to about 0.05 moles.

In an aspect of the invention, α-form crystal of Mirabegron prepared according to the present invention are substantially pure having a chemical purity greater than about 98.5%, or greater than about 99.0%, or greater than about 99.5% by weight as determined using high performance liquid chromatography (HPLC). The α-form crystal of Mirabegron produced by a method of present invention are chemically pure Mirabegron having purity greater than about 99.5% and contain no single impurity in amounts greater than about 0.15%, by HPLC. The α-form crystal of Mirabegron produced by the methods of present invention are chemically pure Mirabegron having purity greater than about 99.8% and contain no single impurity in amounts greater than about 0.1%, by HPLC.

Mirabegron used as the input material for the processes of the present invention is obtained by a process known to a person ordinary skilled in the art. In a specific embodiment, the input material is prepared by practicing the chemistry disclosed in US'532 and US '117 patents or by method illustrated in example-1 or example-2 of the present specification.

In yet another embodiment of the present invention the moisture content of Mirabegron used for the preparation of α-form crystal of Mirabegron of the present invention should not be more than 10% W/W, preferably not more than 7%, preferably not more than 5%, preferably not more than 3% or preferably not more than 1%.

The α-form crystal form of Mirabegron prepared according to the present invention can be used in the preparation of pharmaceutical composition for overactive bladder (OAB) with symptoms of urge urinary incontinence, urgency, and urinary frequency. Such pharmaceutical composition can be prepared using one or more pharmaceutically acceptable carriers, excipients or diluents by methods known in the literature.

Present invention is further illustrated with the following non-limiting examples.

Example-1

Preparation of Mirabegron:

To (R)-2-[2-(4-aminophenyl)-ethylamino]-1-phenyl ethanol hydrochloride (1 Kg) 4000 mL water was added and the reaction mixture was stirred for 10-20 min. at 25-30° C. Thereafter (2-amino-thiazol-4-yl)-acetic acid (480 gm) was added, followed by conc. HCl (240 mL) and the reaction mixture was stirred for 10-20 min. at 25-30° C. A solution of EDC.HCl (687 gm) in water (1 L) was prepared and added to the reaction mixture gradually at 25-30° C. and the reaction mixture was stirred for 60-120 min. After completion of reaction, 6.0% aqueous NaOH was gradually added to the reaction mixture till pH 9-11 is attained and stirred for 30-60 min. at 25-30° C. Thereafter the reaction mass was filtered and washed with water (2×2 L) and suck dried. The wet cake was slurry washed with 15 L of water filtered, washed with water and vacuum dried at 45-50° C. till water content is less than 5% w/w.

Yield=74-100%
HPLC purity=>98.5%

Example-2

Preparation of Mirabegron

To (R)-2-[2-(4-aminophenyl)-ethylamino]-1-phenyl ethanol hydrochloride (1 kg) 4000 mL water was added and the reaction mixture was stirred for 10-20 min. at 25-30° C. Thereafter (2-amino-thiazol-4-yl)-acetic acid (540 gm) was added, followed by conc. HCl (240 mL) and the reaction mixture was stirred for 10-20 min. at 25-30° C. A solution of 1-(3-Dimethylaminopropyl)-3-ethylcarbodiimide hydrochloride (EDC.HCl) (687 gm) in water (1 L) was prepared and added to the reaction mixture gradually at 25-30° C. and the reaction mixture was stirred for 60-120 min. After completion of reaction ethylenediamine tetra acetic acid (EDTA) (0.010 Kg) was added followed by gradual addition of 6.0% aqueous NaOH till pH 9-11 is attained and stirred for 30-60 min. at 25-30° C. Thereafter the reaction mass was filtered and washed with water (2×2 L) and suck dried. The wet cake was slurry washed with 15 L of water filtered, washed with water and vacuum dried at 45-50° C. till water content is less than 5% w/w.

Yield=74-100%
HPLC purity=>98.5%

Example-3

Preparation of α-Form Crystal of Mirabegron (R)-2-(2-aminothiazol-4-yl)-4'-[2-[(2-hydroxy-2-phenylethyl)amino]ethyl]-acetanilide (15 gm) was added to isopropyl alcohol (150 mL) and heated to 70-75° C. to get clear solution. The clear solution was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (11.0 gm).

HPLC purity=99.14%

Example-4

Preparation of α-Form Crystal of Mirabegron (R)-2-(2-aminothiazol-4-yl)-4'-[2-[(2-hydroxy-2-phenylethyl)amino]ethyl]-acetanilide (15 gm) was added to 10% mixture of ethanol in isopropyl alcohol (120 mL) and heated to 70° C. to get clear solution. The clear solution was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (11.3 gm).

HPLC purity=99.05%

Example-5

Preparation of α-Form Crystal of Mirabegron (R)-2-(2-aminothiazol-4-yl)-4'-[2-[(2-hydroxy-2-phenyl-ethyl)amino]ethyl]-acetanilide (1 Kg) was added to mixture of Methanol (2.4 L) in isopropyl alcohol (9.6 L) and heated to 65-70° C. to get clear solution. The clear solution was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (700 gm).

HPLC Purity=>99%

Example-6

Preparation of α-Form Crystal of Mirabegron (R)-2-(2-aminothiazol-4-yl)-4'-[2-[(2-hydroxy-2-phenyl-ethyl)amino]ethyl]-acetanilide (1 Kg) was added to mixture of methanol (2.4 L) in isopropyl alcohol (9.6 L) followed by addition of ethylenediamine tetra acetic acid (EDTA) (0.010 Kg) and butylated hydroxy anisole (BHA) (0.010 Kg). The reaction mixture was heated to 65-70° C. and stirred for 30-40 min. The reaction mixture was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (750 gm).

HPLC Purity=>99%

Example-7

Preparation of α-Form Crystal of Mirabegron (R)-2-(2-aminothiazol-4-yl)-4'-[2-[(2-hydroxy-2-phenyl-ethyl)amino]ethyl]-acetanilide (15 gm) was added to 20% mixture of isopropyl alcohol in acetone (375 mL) and heated to 60° C. to get a clear solution. The clear solution was micron filtered and filtrate was transferred to clean flask. The contents were cooled and stirred for 18 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (4.0 gm).

HPLC Purity=99.36%

Example-8

Preparation of α-Form Crystal of Mirabegron (R)-2-(2-aminothiazol-4-yl)-4'-[2-[(2-hydroxy-2-phenyl-ethyl)amino]ethyl]-acetanilide (15 gm) was added to 50% mixture of dichloromethane in isopropyl alcohol (300 mL) and heated to 45° C. to get clear solution. The clear solution was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (4.4 gm).

Example-9

Preparation of α-Form Crystal of Mirabegron (R)-2-(2-aminothiazol-4-yl)-4'-[2-[(2-hydroxy-2-phenyl-ethyl)amino]ethyl]-acetanilide (1 Kg) was added to mixture of methanol (2.4 L) in isopropyl alcohol (9.6 L) followed by addition of butylated hydroxy anisole (BHA) (0.010 Kg). The reaction mixture was heated to 65-70° C. and stirred for 30-40 min. The reaction mixture was micron filtered and filtrate was transferred to clean flask. The contents were cooled and stirred for 2-3 hr at 25-30° C. and then further cooled to 0-5° C. and stirred for 2-3 hr. The precipitated solid was filtered and dried to yield (R)-2-(2-aminothiazol-4-yl)-4'-[2-[(2-hydroxy-2-phenylethyl) amino] ethyl]-acetanilide (760 gm).

HPLC Purity=>99%

Example-10

Preparation of α-Form Crystal of Mirabegron (R)-2-(2-aminothiazol-4-yl)-4'-[2-[(2-hydroxy-2-phenyl-ethyl)amino]ethyl]-acetanilide (1 Kg) was added to mixture of methanol (2.4 L) in isopropyl alcohol (9.6 L) followed by addition of butylated hydroxy anisole (BHA) (0.010 Kg). The reaction mixture was heated to 65-75° C. and stirred for 30-40 min. The reaction mixture was filtered through celite bed followed by micron filteration. The celite bed and micron filter was washed with hot methanol:isopropanol mixture (2:8; 1.0 L). The filtrate was transferred to a clean flask. The contents were cooled and stirred for 2-3 hr at 25-30° C. and then further cooled to 0-5° C. and stirred for 2-3 hr. The precipitated solid was filtered and dried at 45-50° C. The dried product was multi milled followed by cad milling using #60 mesh QS equivalent 61 followed by sifting using #40 mesh to yield (R)-2-(2-aminothiazol-4-yl)-4'-[2-[(2-hydroxy-2-phenylethyl) amino] ethyl]-acetanilide (760 gm).

HPLC Purity=>99%

The invention claimed is:

1. A process for preparing α-form crystal of Mirabegron comprising the steps of;
   (a) mixing Mirabegron with a mixture of at least two organic solvents selected from the group consisting of alkanol, ketone, chlorinated hydrocarbon, ester and nitrile;
   (b) adding an antioxidant or a chelating agent or both to the mixture of step (a);
   (c) heating the mixture of step (b) to obtain a solution;
   (d) cooling the solution obtained in step (c) to form α-form crystal of Mirabegron;
   (e) isolating the α-form crystal of Mirabegron from step (d);
   (f) drying the isolated α-form crystal of Mirabegron from step (e) under reduced pressure; and
   (g) milling the dried α-form crystal of Mirabegron from step (f); wherein the chelating agent is ethylenediamine tetraacetic acid.

2. The process according to claim 1 wherein the alkanol is selected from the group consisting of methanol, ethanol, propanol, isopropanol and mixtures thereof.

3. The process according to claim 2, wherein the alkanol is a mixture of methanol and isopropanol.

4. The process according to claim 3 wherein the ratio of methanol to isopropanol is 1:4.

5. The process according to claim 1 wherein the antioxidant is selected from the group consisting of butylated hydroxy toluene butylated hydroxy anisole, α-tocopherol, tocopheryl acetate and a mixture of at least two thereof.

6. The process according to claim 5 wherein the antioxidant is butylated hydroxy anisole.

7. The process according to claim 1 wherein the mole ratio of the antioxidant or the chelating agent to that of the Mirabegron is in the range of about 0.01 to about 0.05 moles.

8. The process according to claim 1 wherein the solution of step (c) is obtained by heating the reaction mixture at about 60° C. to about 75° C.

9. The process according to claim 1, wherein the particle size of the α-form crystal of Mirabegron ($d_{90}$) is not more than 75 μm, ($d_{50}$) is between about 5 μm to about 30 μm and ($d_{10}$) is not less than 2 μm.

* * * * *